US010772880B2

(12) United States Patent
Polymeropoulos et al.

(10) Patent No.: US 10,772,880 B2
(45) Date of Patent: *Sep. 15, 2020

(54) METHOD OF TREATMENT WITH TRADIPITANT

(71) Applicant: Vanda Pharmaceuticals Inc., Washington, DC (US)

(72) Inventors: Mihael H. Polymeropoulos, Potomac, MD (US); Louis William Licamele, Potomac, MD (US)

(73) Assignee: VANDA PHARMACEUTICALS INC., Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/430,514

(22) Filed: Jun. 4, 2019

(65) Prior Publication Data

US 2019/0290625 A1 Sep. 26, 2019

Related U.S. Application Data

(63) Continuation of application No. 15/553,394, filed as application No. PCT/US2016/021015 on Mar. 4, 2016.

(60) Provisional application No. 62/232,644, filed on Sep. 25, 2015, provisional application No. 62/128,472, filed on Mar. 4, 2015.

(51) Int. Cl.
  *A61K 31/444* (2006.01)
  *A61K 31/4439* (2006.01)
  *A61P 17/04* (2006.01)
  *A61K 9/00* (2006.01)

(52) U.S. Cl.
  CPC .......... *A61K 31/444* (2013.01); *A61K 9/0053* (2013.01); *A61K 31/4439* (2013.01); *A61P 17/04* (2018.01)

(58) Field of Classification Search
  CPC .................................................. A61K 31/444
  See application file for complete search history.

(56) References Cited

U.S. PATENT DOCUMENTS

| 5,585,385 A | 12/1996 | Natsugari et al. |
| 7,320,994 B2 * | 1/2008 | Amegadzie .......... C07D 249/06 514/359 |
| 7,799,782 B2 | 9/2010 | Munson et al. |
| 2007/0078166 A1 | 4/2007 | Borghese et al. |
| 2010/0056795 A1 | 3/2010 | Kobierski et al. |
| 2014/0378521 A1 | 12/2014 | Zhang et al. |

FOREIGN PATENT DOCUMENTS

WO 2014209962 A1 12/2014

OTHER PUBLICATIONS

Trower, Michael K.; "Neurokinin-1 receptor antagonist orvepitant is an effective inhibitor of itch-associated response in a Mongolian gerbil model of scratching behaviour"; Experimental Dermatology; 2014; 23; pp. 853-864.
Santini, Daniele et al.; "Aprepitant for management of severe pruritus related to biological cancer treatments: a pilot study"; The Lancet; vol. 13; Oct. 2012; Published online Sep. 18, 2012; pp. 1020-1024.
FDA; "Guidance for Industry Exposure-Response Relationships—Study Design, Data Analysis, and Regulatory Applications"; Published Apr. 2003; pp. 1-28.
Sun, Zhigang et al.; "Particle Size Specifications for Solid Oral Dosage Forms: A Regulatory Perspective"; American Pharmaceutical Review; Published May 1, 2010; pp. 1-9.
International Search Report & Written Opinion for International Application No. PCT/US2016/021015 dated Jun. 2, 2016, 14 pages.
George et al. "Supporting Online Material for Neurokinin 1 Receptor Antagonism as a Possible Therapy for Alcoholism", Science, vol. 319, No. 2869, dated Mar. 14, 2008, 14 pages.
George et al. "Neurokinin 1 Receptor Antagonism as a Possible Therapy for Alcoholism", Science, vol. 319, No. 2869, dated Mar. 14, 2008, 9 pages.
Stander et al. "Targeting the Neurokinin Receptor 1 with Aprepitant: A Novel Antipruritic Strategy", Plos One, vol. 5., No. 6, Jan. 1, 2010, 6 pages.
Tauscher et al. "Development of the 2nd generation neurokinin-1 receptor antagonist LY686017 for social anxiety disorder", European Neuropsychopharmacology, Elsevier Science Publishers BV, Amsterdam, NL, vol. 20, No. 2, Feb. 1, 2010, 8 pages.
Sadick Research Group; "Tradipitant in Treatment-Resistant Pruritus Associated With Atopic Dermatitis"; ClinicalTrails.gov Identifier NCT02672410; First Received Feb. 1, 2016; last Updated Feb. 2, 2016; accessed on Feb. 11, 2016; pp. 3; <https://clinicaltrials.gov/ct2/show/study/NCT02672410?TERM=TRADIPITANT&RANK=3>.
Notice of Reasons for Rejection for corresponding JP Application No. 2017-546704 dated Jan. 14, 2020, 7 pages.
Anonymous, "History of Changes for Study: NCT02004041: Proof of Concept of VLY-686 in Subjects With Treatment-Pruritus Associated with Atopic Dermatitis," U.S. National Library of Medicine, ClinicalTrials.gov archive, retrieved from: https://clinicaltrials.gov/ct2/history/NCT02004041?A=4&B=4&C=merged on Dec. 16, 2019, 9 pgs.
Anonymous, "History of Changes for Study: NCT01919944: Study of Itch Control by VLY-686 in Healthy Volunteers After Intradermal Injections of Substance P," U.S. National Library of Medicine, ClinicalTrials.gov archive, retrieved from https://clinicaltrials.gov/ct2/history/NCT01919944?A=5&B=5&C=merged on Dec. 16, 2019, 9 pgs.

* cited by examiner

*Primary Examiner* — Rei Tsang Shiao
(74) *Attorney, Agent, or Firm* — Hoffman Warnick LLC

(57) ABSTRACT

This application relates to a method of treatment with tradipitant, and more particularly, to a method of treatment of pruritus with tradipitant.

13 Claims, 2 Drawing Sheets

METHOD OF TREATMENT WITH TRADIPITANT

CROSS REFERENCE TO RELATED APPLICATIONS

This application is a continuation of co-pending U.S. application Ser. No. 15/553,394, filed 24 Aug. 2017, which is a US national stage under 35 USC § 371 of international patent Application No. PCT/US2016/021015, filed 4 Mar. 2016, which in turn claims the benefit of U.S. Provisional Applications No. 62/128,472, filed 4 Mar. 2015, and No. 62/232,644, filed 25 Sep. 2015, each of which is incorporated herein as though fully set forth.

BACKGROUND

Chronic pruritus affects millions of people worldwide and represents a serious and unmet medical need. The itch sensation is believed to be induced at least in part through the action of the endogenous neuropeptide substance P (SP), through the binding at NK-1Rs expressed on multiple skin cells.

The NK-1R is expressed throughout different tissues of the body, with major activity found in neuronal tissue. SP and NK-1R interactions in neuronal tissue regulate neurogenic inflammation locally and the pain perception pathway through the central nervous system. Other tissues, including endothelial cells and immune cells, have also exhibited SP and NK-1R activity. The activation of NK-1R by the natural ligand SP is involved in numerous physiological processes, including the perception of pain, behavioral stressors, cravings, and the processes of nausea and vomiting. An inappropriate over-expression of SP either in nervous tissue or peripherally could result in pathological conditions such as substance dependence, anxiety, nausea/vomiting, and pruritus. An NK-1R antagonist may possess the ability to reduce this over-stimulation of the NK-1R, and as a result address the underlying pathophysiology of the symptoms in these conditions.

Tradipitant is a neurokinin-1 receptor antagonist formerly known as VLY-686, having the chemical names 2-[1-[[3,5-bis(trifluoromethyl)phenyl]methyl]-5-(4-pyridinyl)-1H-1,2,3-triazol-4-yl]-3-pyridinyl](2-chlorophenyl)-methanone and {2-[1-(3,5-Bistrifluoromethylbenzyl)-5-pyridin-4-yl-1H-[1,2,3]triazol-4-yl]-pyridin-3-yl}-(2-chlorophenyl)-methanone, and the following chemical structure:

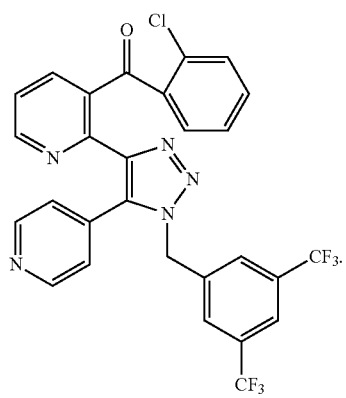 [SMILES: O=C(c1ccccc1Cl)c1cccnc1-c1nnn(Cc2cc(C(F)(F)F)cc(C(F)(F)F)c2)c1-c1ccncc1]

Tradipitant is disclosed in U.S. Pat. No. 7,320,994, and contains six main structural components: the 3,5-bis-trifluoromethylphenyl moiety, two pyridine rings, the triazol ring, the chlorophenyl ring and the methanone. Crystalline Forms IV and V of tradipitant are disclosed in U.S. Pat. No. 7,381,826. A process for synthesizing tradipitant is disclosed in U.S. Pat. No. 8,772,496.

BRIEF DESCRIPTION OF THE INVENTION

A first aspect of the disclosure provides a method of administering tradipitant to a patient in need thereof which comprises internally administering to the patient tradipitant in an amount and at a frequency of administration sufficient to achieve and to maintain a plasma concentration of >100 ng/mL.

A second aspect of the disclosure provides a method of administering tradipitant to a patient in need thereof which comprises internally administering an effective amount of tradipitant to the patient. The effective amount may be, e.g., 100 to 400 mg/day, 100 to 300 mg/day, or 100 to 200 mg/day. The effective amount may be administered twice daily, i.e., 50 to 200 mg bid, 50 to 150 mg bid, 50 to 100 mg bid, or about 85 mg bid.

A third aspect of the disclosure provides a use of tradipitant for the treatment of pruritus by internally administering to a patient suffering from pruritus by internally administering to the patient tradipitant in an amount and at a frequency of administration sufficient to achieve and to maintain a plasma concentration of >100 ng/mL, i.e., an effective amount of tradipitant.

A fourth aspect of the disclosure provides a use of tradipitant for the preparation of a medicament for the treatment of pruritus by internally administering to the patient tradipitant in an amount and at a frequency of administration sufficient to achieve and to maintain a plasma concentration of >100 ng/mL, i.e., an effective amount, e.g., an amount of 85 mg bid, 85 mg qd, 100 mg qd, or other dosing regimen.

In further aspects of the invention, the dose can be 85 to 170 mg/day. This may be, e.g., 85 mg bid, 85 mg qd, 100 mg qd, or 100 mg bid.

DETAILED DESCRIPTION OF THE DISCLOSURE

Figure 1:
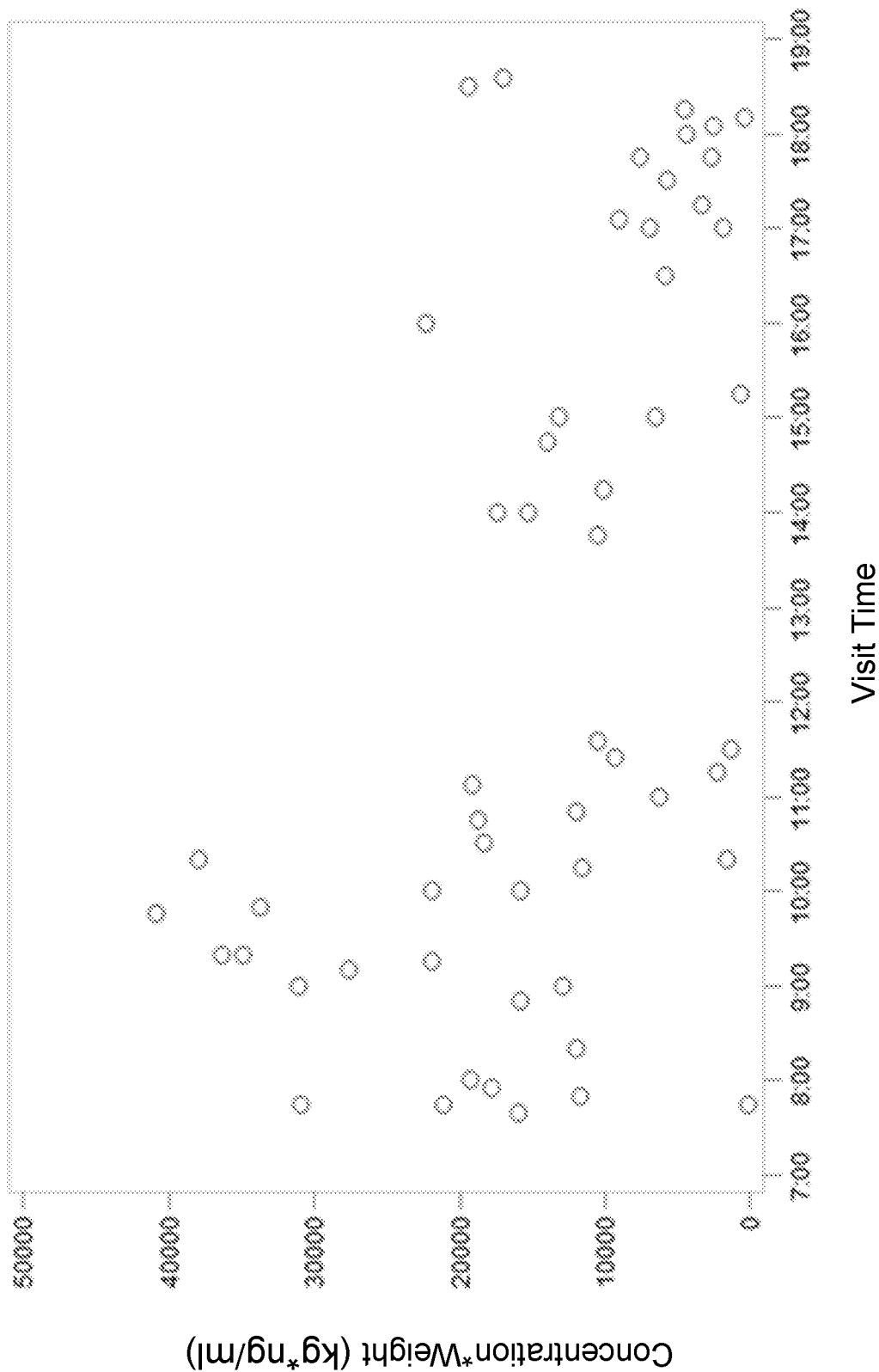
FIG. 1 provides a scatter plot of serum levels of tradipitant, showing concentration weight vs. visit time.
Figure 2:
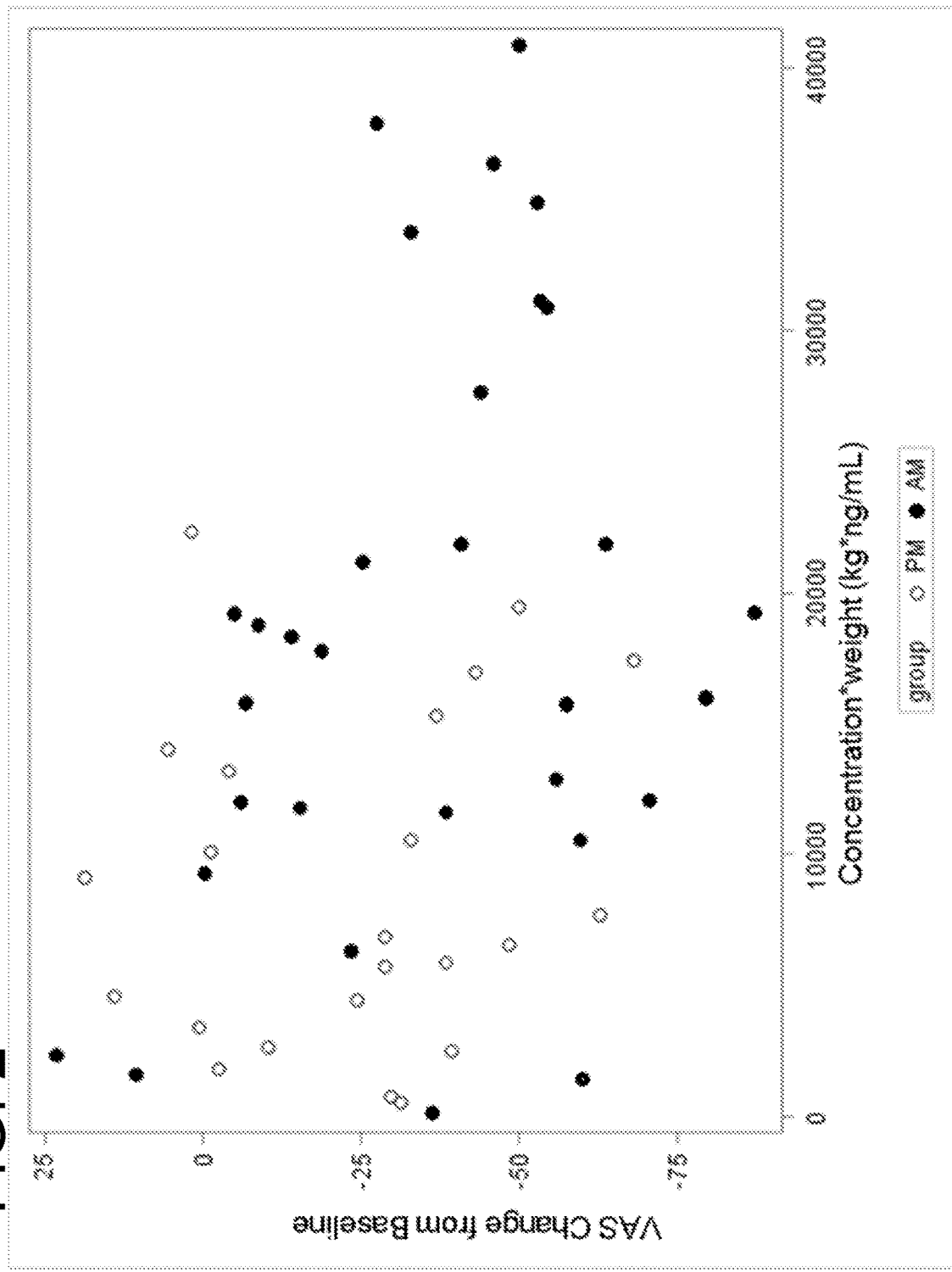
FIG. 2 provides a scatter plot of VAS change vs. concentration-weight of tradipitant (Spearman correlation P-value=0.0204).

At least one embodiment of the present invention is described below in reference to its application in connection with the use of tradipitant for the treatment of chronic pruritus. Although embodiments of the invention are illustrated relative to specific dosing regimens, e.g., 100 mg qd, 85 mg bid, and 85 mg qd, it is understood that the teachings are equally applicable to other dosing regimens, e.g., 100 to 400 mg/day, 100 to 300 mg/day, 100 to 200 mg/day, or about 85-170 mg/day, which may be administered as, e.g., 50 to 200 mg bid, 50 to 150 mg bid, 50 to 100 mg bid, or about 85 mg bid.

As used herein, the term "patient" refers to a mammal that is afflicted with one or more disorders ameliorated by administration of tradipitant, e.g., pruritus. Guinea pigs, dogs, cats, rats, mice, horses, cattle, sheep, and humans are examples of mammals within the scope of the meaning of the term. It will be understood that the most preferred patient is a human.

It is also recognized that one skilled in the art may affect the disorders by treating a patient presently afflicted with the disorders or by prophylactically treating a patient afflicted with the disorders with an effective amount of tradipitant. Thus, the terms "treatment" and "treating" are intended to refer to all processes wherein there may be a slowing, interrupting, arresting, controlling, or stopping of the progression of the disorders described herein, and is intended to include prophylactic treatment of such disorders, but does not necessarily indicate a total elimination of all disorder symptoms.

As used herein, the term "effective amount" of tradipitant refers to an amount that is effective in treating the disorders described herein.

With regard to dosing, "qd" refers to dosing once per day; bid dosing typically means dosing once in the morning and once in the evening, generally no less than about 8 hours or more than about 16 hours apart, e.g., 10 to 14 hours or 12 hours (Q12H).

The skilled artisan will appreciate that additional preferred embodiments may be selected by combining the preferred embodiments above, or by reference to the examples given herein.

Example 1

A phase II proof of concept clinical study (Study ID VP-VLY-686-2101, "Proof of Concept of VLY-686 in Subjects With Treatment-Resistant Pruritus Associated With Atopic Dermatitis") was conducted, investigating the safety and efficacy of tradipitant as a monotherapy in the treatment of chronic pruritus in patients with atopic dermatitis.

Despite a highly significant and clinically meaningful improvement from baseline by tradipitant (40.5 mm improvement from baseline, p<0.0001) as measured on a 100 mm unit Visual Analog Scale (VAS) for itch, a very high placebo effect (36.5 mm improvement from baseline, p<0.0001) on the change from baseline led to no statistical difference from placebo. However, subsequent analysis of population PK samples across all patients in the study revealed significant and clinically meaningful responses across multiple outcomes evaluated in individuals with higher levels of tradipitant exposure at the time of their pruritus assessments.

The pre-specified primary endpoint of the Phase II proof of concept clinical study was the change from baseline on the Visual Analog Scale (VAS) for itch. Due to high placebo effect, there was no significant difference from placebo on this pre-specified endpoint. However, in subsequent analyses it has been discovered that there is an exposure response relationship. It has further been observed that there is a significant and clinically meaningful response across several pruritus related outcomes evaluated in individuals with higher blood plasma levels of tradipitant. Based on the data examined across the study, lower blood plasma levels of tradipitant may be below a threshold of efficacy to ameliorate the itch sensation in patients.

Methods

In the study, patients with a Visual Analog Scale (VAS) score of greater than 70 mm during one of the two days preceding inclusion into the study were randomized to receive orally either 100 mg of tradipitant (N=34) or placebo (N=35) once a day in the evening. In the tradipitant arm of the study, tradipitant was orally administered to patients in capsules with standard excipients in an amount of 100 mg in the evening. Clinical assessments were made after 3 or 4 weeks of daily treatment, or at both 3 weeks and 4 weeks, each assessment being done in the morning of the day after last treatment or in the afternoon of the day after last treatment. The tradipitant was administered in an immediate release form comprising tradipitant and pharmaceutically acceptable excipients in a capsule. The tradipitant particle size was approximately: $D_{10}$: <5 um, $D_{50}$: <10 um, and $D_{90}$: <25 um, wherein $D_{10}$ means that 10% of the particles are of the indicated mean particle size, $D_{50}$ means that 50% of the particles are of the indicated mean particle size, and $D_{90}$ means that 90% of the particles are of the indicated mean particle size.

Baseline VAS scores were 76.1 and 77.2 for the tradipitant and placebo arms respectively. Efficacy was evaluated through a number of clinical research instruments. In addition, at the time of efficacy evaluation blood samples were collected for PK analysis in order to determine the plasma levels of tradipitant.

Results

A PK-PD (pharmacokinetic-pharmacodynamics) analysis in the tradipitant treatment arm showed a significant correlation between blood levels of tradipitant and the VAS change from baseline (p<0.05). Individuals with higher circulating levels of tradipitant at the time of the efficacy evaluation demonstrated higher magnitude of response. A separate PK analysis of the time of pruritus assessment revealed that approximately half the patients in the study came in for morning (AM group, ~12 hours post-dose) visits for their pruritus assessments and that these patients also had higher blood levels of tradipitant than those who came in the afternoon (PM group, ~18 hours post-dose).

The average plasma concentrations of tradipitant across AM and PM-evaluated patients were between about 125 ng/mL and about 225 ng/mL. Patients evaluated in the afternoons (PM) (mean=about 20 hours post last administration) tended to have lower plasma concentrations of tradipitant than patients evaluated in the mornings (AM) (mean=about 15 hours post last administration). The average plasma concentration in the PM group was about 125 ng/mL, and the average plasma concentration in the AM group was about 225 ng/mL, the difference being largely attributable to the length of time post administration. More significantly, the results show a correlation between plasma concentration and efficacy, whereby patients in whom the plasma concentrations were >100 ng/mL (e.g., about 125 ng/mL or greater, about 150 ng/mL or greater, about 175 ng/mL or greater, about 200 ng/mL or greater, or about 225 ng/mL or greater) tended to show greater efficacy than patients with lower plasma concentrations.

A further analysis of the AM group revealed significant and clinically meaningful effects of tradipitant as compared to placebo and is shown in Table 1. Higher concentrations of tradipitant were associated with higher efficacy in treating chronic pruritus in the study. A similar analysis in the PM group showed no significant differences between tradipitant and placebo.

TABLE 1

Group efficacy analysis of pruritus measures

|  | AM | | | | PM | | | |
| --- | --- | --- | --- | --- | --- | --- | --- | --- |
|  | Tradipitant N = 18 | Placebo N = 17 | Diff | P-value | Tradipitant N = 13 | Placebo N = 11 | Diff | P-value |
| Primary |  |  |  |  |  |  |  |  |
| VAS Average change | −54 | −30.3 | −23.7 | 0.007 | −28.8 | −34.6 | 5.82 | 0.6701 |
| Secondary |  |  |  |  |  |  |  |  |
| VAS Worst change | −47.9 | −26 | −21.9 | 0.0302 | −32.3 | −41.3 | 8.99 | 0.5153 |
| VRS change | −1.46 | −0.67 | −0.79 | 0.0496 | −1.29 | −1.16 | −0.13 | 0.7881 |
| DLQI change | −2.52 | −2.87 | 0.35 | 0.8458 | −5.45 | −3.56 | −1.89 | 0.2423 |
| PBI | 1.47 | 0.73 | 0.74 | 0.0393 | 1.01 | 1.4 | −0.39 | 0.4696 |
| CGIC | 2.46 | 3.61 | −1.15 | 0.0497 | 2.47 | 2.29 | 0.19 | 0.7452 |
| SCORAD change | −9.58 | −4.36 | −5.23 | 0.0027 | −6.29 | −7.18 | 0.88 | 0.7061 |

Table 1 abbreviations: Visual Analog Scale (VAS), Verbal Rating Scale (VRS), Dermatology Life Quality Index (DLQI), Clinical Global Impression of Change (CGI-C), Patient Benefit Index (PBI), SCORing Atopic Dermatitis Index (SCORAD).

This data is consistent with the hypothesis that tradipitant, an NK-1R antagonist, may offer symptomatic relief in patients with pruritus (VAS, VRS, SCORAD subjective). Endpoints were also collected in the study that correspond to the underlying disease (SKINDEX, SCORAD objective, EASI and DLQI). These results did not show any significant difference from placebo which would be expected from a drug targeting the symptom of itch in a short-term 4-week study. Importantly, as pruritus, the intractable itching associated with atopic dermatitis, is the major complaint of patients, the effects that were also seen in the CGI-C scale and the PBI scales suggest a recognizable overall clinically meaningful effect from both the clinician and the patient perspective.

Conclusions

These data support the premise that in patients suffering pruritus, e.g., pruritus associated with atopic dermatitis, patients can be treated by orally administering tradipitant, e.g., Form IV or Form V (or a pharmaceutically acceptable salt thereof) in amounts and at a dosing frequency required to achieve plasma concentrations of at least about 100 ng/mL, e.g., 125 ng/mL or greater, 150 ng/mL or greater, 175 ng/mL or greater, 200 ng/mL or greater, or 225 ng/mL or greater. Such plasma concentration levels can be achieved, e.g., by orally administering the tradipitant in immediate release solid dosage forms once per day at a higher dose or in immediate release forms with improved bioavailability or in controlled release forms, or by orally administering the tradipitant multiple times per day, e.g., twice or more times per day, at a lower dose in immediate release or controlled release forms. While the study data show that an effective plasma concentration can be achieved at about 12-18 hours, e.g., about 15 hours, post treatment with 100 mg/day tradipitant in solid form in immediate release capsules, it will be appreciated that it may be possible to achieve effective plasma concentrations using different doses and/or different formulations, including but not limited to controlled release formulations.

In conclusion, while the study failed to show an overall effect of the predefined dose of tradipitant for this study, primarily due to the large placebo effect, the study demonstrated a PK-response relationship as well as significant benefits in the group of patients that were evaluated at the time of higher blood concentrations of tradipitant. In this study tradipitant 100 mg qd was well-tolerated and the adverse event profile was mild and similar to placebo.

Treatment of a patient can be continued until the patient's symptoms of pruritus are ameliorated or eliminated, e.g., ameliorated such that the patient is able to function more or less normally during wake time hours and sleep more or less normally during sleep time hours.

As discussed above, data indicate that in patients suffering pruritus, e.g., pruritus associated with atopic dermatitis, patients can be treated by orally administering tradipitant. Further studies have demonstrated the safety and efficacy of various dosing regimens.

Example 2

In one study, healthy subject participants were orally administered 85 mg tradipitant on study day 3, and then 85 mg tradipitant Q12H on study days 4-16. Plasma concentration levels of tradipitant were measured on each of day 3, day 7, and day 11.

This study illustrated that administration of 85 mg tradipitant qd (on day 3) produced an average plasma concentration over hours 0-12 that was about 50% of the plasma concentration observed in the PM group in Example 1. On days 7 and 11, the average plasma concentration over hours 0-12 following administration of 85 mg bid (specifically, Q12H) tradipitant was about 150% of the plasma concentration observed in the PM group in Example 1. The average plasma concentration over hours 0-12 at each point was determined by dividing the AUC for hours 0-12 (in (hr.)× (ng/mL)) by 12 hours.

These results indicate that in patients suffering pruritus, e.g., pruritus associated with atopic dermatitis, patients can be treated by orally administering tradipitant, e.g., Form IV or Form V (or a pharmaceutically acceptable salt thereof) in an amount of 85 mg bid, e.g., 85 mg Q12H, in order to achieve plasma concentrations that are greater than the 125 ng/mL observed in the PM group in Example 1.

Embodiments

In addition to other illustrative embodiments, this invention can be seen to comprise one or more of the following illustrative embodiments:

1. A method of administering tradipitant to a patient in need thereof which comprises internally administering to the patient tradipitant in an amount and at a frequency of administration sufficient to achieve and to maintain a plasma concentration of at least about 100 ng/mL, e.g., about 125 ng/mL or greater, about 150 ng/mL or greater, about 175 ng/mL or greater, about 200 ng/mL or greater, or about 225 ng/mL or greater for the duration of the treatment regimen.

2. A method of administering tradipitant to a patient in need thereof which comprises internally administering to the patient tradipitant in an amount and at a frequency of administration sufficient to achieve and to maintain a plasma concentration equal to or greater than the plasma concentration in a study population of patients 12 to 18 hours following oral administration of 100 mg tradipitant in an immediate release form for the duration of the treatment regimen.

3. The method of embodiment 1 or 2 wherein the tradipitant is orally administered in a solid immediate release form such as a capsule or tablet comprising tradipitant and one or more pharmaceutically acceptable excipients.

4. The method of embodiment 1 or 2 wherein the tradipitant is orally administered in a solid controlled release form such as a capsule or tablet comprising tradipitant and one or more pharmaceutically acceptable excipients.

5. A method of administering tradipitant ({2-[1-(3,5-bis-trifluoromethylbenzyl)-5-pyridin-4-yl-1H-[1,2,3]triazol-4-yl]-pyridin-3-yl}-(2-chlorophenyl)-methanone) to a patient in need thereof which comprises orally administering to the patient tradipitant in a solid immediate release form such as a capsule or tablet comprising tradipitant and one or more pharmaceutically acceptable excipients twice daily in an amount of 100 to 400 mg/d, 100 to 300 mg/d, or 100 to 200 mg/d of tradipitant.

6. A method of administering tradipitant ({2-[1-(3,5-bis-trifluoromethylbenzyl)-5-pyridin-4-yl-1H-[1,2,3]triazol-4-yl]-pyridin-3-yl}-(2-chlorophenyl)-methanone) to a patient in need thereof which comprises orally administering to the patient tradipitant once daily in a solid immediate release form such as a capsule or tablet comprising tradipitant and one or more pharmaceutically acceptable excipients in an amount of 150 to 400 mg/d, 150 to 300 mg/d, or 150 to 200 mg/d of tradipitant.

7. The method of any of the preceding embodiments wherein the patient is being treated with tradipitant for pruritus.

8. The method of any of the preceding embodiments wherein the patient is being treated with tradipitant for atopic dermatitis and/or chronic pruritus.

9. The method of any of the preceding embodiments wherein the tradipitant is in crystalline Form IV or Form V.

10. Tradipitant for use in any of the preceding methods of treatment.

11. A pharmaceutical composition comprising tradipitant for use in any of the preceding methods.

12. Tradipitant for use in the manufacture of a pharmaceutical composition comprising tradipitant for use in any of the preceding methods.

13. A method of administering tradipitant to a patient in need thereof which comprises internally administering to the patient tradipitant in an amount and at a frequency of administration sufficient to achieve and to maintain a plasma concentration of >100 ng/mL.

14. The method of embodiment 13, wherein the plasma concentration of >100 ng/mL is selected from the group consisting of: 125 ng/mL or greater, 150 ng/mL or greater, 175 ng/mL or greater, 200 ng/mL or greater, and 225 ng/mL or greater for the duration of the treatment regimen.

15. The method of embodiment 13, wherein the internally administering step is orally administering.

16. A method of administering tradipitant to a patient in need thereof which comprises internally administering to the patient tradipitant in an amount of 85-170 mg/day.

17. The method of embodiment 16, further comprising internally administering to the patient tradipitant in an amount of 85 mg qd.

18. The method of embodiment 16, further comprising internally administering to the patient tradipitant in an amount of 85 mg bid.

19. The method of embodiment 16, further comprising internally administering to the patient tradipitant in an amount of 100 mg qd.

20. A method of administering tradipitant to a patient in need thereof which comprises internally administering to the patient tradipitant in an amount of 50 to 200 mg bid.

21. A method of administering tradipitant to a patient in need thereof which comprises internally administering to the patient tradipitant in an amount of 50 to 150 mg bid.

22. A method of administering tradipitant to a patient in need thereof which comprises internally administering to the patient tradipitant in an amount of 50 to 100 mg bid.

23. The method of any of embodiments 13-22, wherein the tradipitant is being administered to treat pruritus.

24. Tradipitant for use in the treatment of pruritus by internally administering to a patient suffering from pruritus by internally administering to the patient tradipitant in accordance with the method of any of embodiments 13-22.

25. Tradipitant for use in the preparation of a medicament for the treatment of pruritus by internally administering to the patient tradipitant in accordance with the method of any of embodiments 13-19.

From the above, it is apparent that the dose can be one that results in plasma concentration at about 12 hours post-dose of about 100 ng/mL to about 225 ng/mL, including e.g., about 125, about 150, about 175, or about 200 ng/mL.

Tradipitant can be administered for the treatment of pruritis in an immediate release form at a dose of 50 to 100 mg qd, e.g., 85 mg qd or 100 mg qd. Twice daily (bid) dosing of tradipitant in immediate release forms at 50 to 100 mg allows achievement and maintenance of the target plasma concentrations throughout a 24 hour period. Accordingly, administration of, e.g., 85 mg (immediate release) bid provides greater and/or more sustained relief from the symptoms of pruritis than qd dosing (immediate release) at the same or a higher dose.

We claim:

1. A method of treating a disease or condition responsive to tradipitant therapy in an individual in need of treatment for such disease or condition, wherein the disease or condition responsive to tradipitant therapy is pain, a behavioral stressor, craving, nausea, vomiting, substance dependence, anxiety, pruritus, or atopic dermatitis comprising:

administering about 170 mg/day of tradipitant to the individual for such time as required to achieve and maintain a tradipitant plasma concentration of at least about 175 ng/mL during said treatment.

2. The method of claim 1, wherein the administering step further comprises orally administering.

3. The method of claim 1, wherein the administering further comprises tradipitant dosing of 85 mg bid.

4. A method of administering tradipitant to an individual, afflicted with a disorder that is pain, a behavioral stressor, craving, nausea, vomiting, substance dependence, anxiety, pruritus, or atopic dermatitis, which comprises:
orally administering to the individual tradipitant in a solid immediate release form comprising one or more pharmaceutically acceptable excipients, and tradipitant at a dose of 150 to 400 mg/day.

5. The method of claim 4, wherein the solid immediate release form is a capsule or a tablet.

6. The method of claim 4, wherein the dose of tradipitant is 150 to 400 mg once daily (qd).

7. The method of claim 4, wherein the dose of tradipitant is 75 to 200 mg twice daily (bid).

8. The method of claim 4, wherein the dose of tradipitant is 85 mg twice daily (bid) or 100 mg bid.

9. The method of claim 4, wherein the oral administration is continued to achieve and maintain an effective plasma concentration of tradipitant,
wherein the effective plasma concentration of tradipitant is about 150 ng/mL or greater during treatment.

10. The method of claim 4, wherein the disorder is caused by an over-expression of substance P or over-stimulation of the neurokinin-1 (NK-1) receptor and ameliorated by administration of tradipitant.

11. The method of claim 9, wherein the effective plasma concentration of tradipitant is about 175 ng/mL or greater.

12. The method of claim 11, wherein the effective plasma concentration of tradipitant is about 200 ng/mL or greater.

13. The method of claim 12, wherein the effective plasma concentration of tradipitant is about 225 ng/mL or greater.

* * * * *